US006627857B1

(12) United States Patent
Tanner et al.

(10) Patent No.: US 6,627,857 B1
(45) Date of Patent: Sep. 30, 2003

(54) ILLUMINATING CANDLE WARMING APPARATUS

(75) Inventors: Brent Robert Tanner, Salt Lake City, UT (US); Greg Gerard Jacobson, Kaysville, UT (US)

(73) Assignee: Park Cities Capital, L.L.C., Salt Lake City, UT (US)

( * ) Notice: Subject to any disclaimer, the term of this patent is extended or adjusted under 35 U.S.C. 154(b) by 0 days.

(21) Appl. No.: 10/197,013

(22) Filed: Jul. 18, 2002

Related U.S. Application Data

(60) Provisional application No. 60/379,094, filed on May 9, 2002.

(51) Int. Cl.$^7$ ................ H05B 3/68; F24F 6/00
(52) U.S. Cl. ................ 219/445.1; 392/390; 392/391
(58) Field of Search ................ 219/443.1, 445.1, 219/446.1, 447.1, 465.1, 490, 507, 518, 520, 548; 392/390, 391, 392, 393

(56) References Cited

U.S. PATENT DOCUMENTS

| | | | | |
|---|---|---|---|---|
| 2,469,656 A | | 5/1949 | Lienert ................ 219/45 |
| 3,748,464 A | | 7/1973 | Andeweg ................ 422/4 |
| 3,780,260 A | * | 12/1973 | Elsner ................ 392/392 |
| 3,813,501 A | * | 5/1974 | Meletti et al. ........ 191/12.2 R |
| 3,876,861 A | * | 4/1975 | Wightman et al. ....... 219/458.1 |
| 4,330,702 A | * | 5/1982 | Cheng ................ 219/492 |
| 4,399,351 A | * | 8/1983 | Koff ................ 219/433 |
| 5,032,360 A | | 7/1991 | Houston ................ 240/108 |
| 5,395,233 A | | 3/1995 | Karp ................ 431/289 |
| 5,434,386 A | * | 7/1995 | Glenn et al. ................ 219/483 |
| 5,647,052 A | * | 7/1997 | Patel et al. ................ 392/390 |
| 5,651,942 A | | 7/1997 | Christensen ................ 422/125 |
| 5,744,106 A | | 4/1998 | Eagle ................ 422/306 |
| 6,106,786 A | | 8/2000 | Akahoshi ................ 422/124 |
| 6,196,706 B1 | | 3/2001 | Cutts ................ 362/392 |
| 6,354,710 B1 | | 3/2002 | Nacouzi ................ 362/96 |

* cited by examiner

Primary Examiner—Sang Paik
(74) Attorney, Agent, or Firm—Christopher L. Johnson; Kirton & McConkie

(57) ABSTRACT

Disclosed is a hot plate warming apparatus adapted to warm a candle or other object resting thereon, as well as to provide illumination that simulates the effects of a lighted burning candle. The apparatus may include an adjustable cord apparatus, a light source, and/or a component enabling attachment of other peripheral components. The light source is positioned proximal to the hot plate for providing illumination to an object or substance resting on the hot plate or housing. The adjustable cord apparatus provides electricity to the warming apparatus while allowing a user to alter the length of the cord that is extending from the warming apparatus. The apparatus also comprises a blower to facilitate heating of a candle placed thereon, as well as to cause scented particles emanating from the melted wax or wax-like substance to be better dispersed or dissipated into the surrounding air. The attachment component permits additional peripheral components or materials to be removably coupled to the warming apparatus, such as interchangeable face plates, covers, craft objects, or module objects.

64 Claims, 9 Drawing Sheets

ILLUMINATING CANDLE WARMING APPARATUS

RELATED APPLICATIONS

This application claims priority to U.S. Provisional Patent Application Serial No. 60/379,094 filed on May 9, 2002 and entitled, "Illuminating Candle Warming Apparatus."

BACKGROUND

1. Field of the Invention

The present invention relates to a warming apparatus. More particularly, the present invention relates to a warming apparatus adapted to warm a substance, such as a scented candle or other object resting thereon, the apparatus configured to include one or more of an adjustable cord apparatus, a light source for illuminating a candle, or auxiliary attachment means for attaching decorative or functional items.

2. Background of the Invention and Related Art

Warming apparatuses, such as hot plates, are adapted to provide heat to an object or substance in contact therewith. A vast array of uses and configurations of warming apparatuses have been developed. Current warming apparatuses range from the simple wire coil heaters for warming food to the composite ceramic electromechanical assemblies used in complex manufacturing.

In recent years, warming device or hot plate technology has been adapted to provide an alternative means of heating scented candles. Scented candles have become enormously popular sale items in boutiques, gift stores, craft centers, and even gun shows. Manufacturers and retailers offer scented candles in a variety of configurations and aromas. Scented candles are typically sold in glass or ceramic containers. The container provides both a means of controlling wax loss and as decorative packaging for the candle. When a user lights the wick of the scented candle, heat from the combustion of the wick slowly melts the candle wax and heats the perfume or other substance responsible for producing the desired scent. Once the wax reaches a molten state, the scented particles are released or escape from the wax or other candle mediums.

Although popular and pleasant, there are a number drawbacks to burning candles as an aroma-delivery device. The open flame of a candle can create a fire risk when burned in a user's home. Additionally, the combustion of the wick and wax consumes a large percentage of the aroma contained in the wax. Waxy residues emitted by the burning candle often become deposited on nearby walls, drapes, furniture, carpet, and ventilation systems. Such residues can be unsightly, may cause damage, are dangerous, and are not easily removed. To provide an alternative method of releasing the aroma from scented candles, some have used a simple hot plate to provide a heating mechanism for melting the wax without requiring combustion of the candle wax or wick. Because the hot plate obviates the need to burn the candle wick, the wax is itself not depleted or emitted into the air. Only the scent is emitted into the air. Even when heated to liquification, little or no wax is emitted into the air.

FIG. 1 illustrates a simple candle warming apparatus 10 adapted for warming scented candles. Warming apparatus 10 comprises a hot plate 12, a housing 14, a switch 16, and a cord 18. The hot plate 12 is sized so as to warm a standard sized scented candle resting thereon. The housing 14 is adapted to surround the hot plate 12 while providing a covering to the internal wiring and internal heating element of the warming apparatus 10. The switch 16 is used to selectively activate and deactivate the hot plate 12. The cord 18 is of a standard length and provides an electrical connection to a standard AC outlet, thus providing the energy needed to heat the hot plate 12. The candle warming apparatus 10 is substantially similar to coffee mug warming devices.

The candle warming apparatus 10, while providing a mechanism to heat a scented candle, nevertheless suffers from several deficiencies. First, although capable of melting the candle wax so as to cause the emission of aroma therefrom, the soft, warm, ambient glow of the lit candle, preferred by many candle enthusiasts, is absent. As a result, the candle warming apparatus 10, while releasing the aroma of the candle, provides an inadequate alternative to an actual burning candle for many candle lovers. Second, the cord 18 is of a fixed length and is located in a fixed location. As a result, in those cases where the entire cord length is not needed, it can provide an aesthetically displeasing effect. Moreover, a cord left to dangle or with excessive slack can cause a hazard of being snagged or looped around a person's foot (e.g., a child or careless adult), thereby potentially causing the warming apparatus 10 and candle to fall to the ground. Third, no mechanism is provided for varying the temperature of the warming apparatus 10 in order to account for variations in the melting temperature of different waxes used to make scented candles. In general, because the warming apparatus 10 is merely an adapted coffee mug warmer, it lacks a variety of desirable features geared to the serious scented candle burning enthusiast.

Accordingly, an improved warming apparatus in multiple embodiments and comprising one or more improved features is disclosed and claimed herein.

SUMMARY AND OBJECTS OF THE INVENTION

In accordance with the invention as embodied and broadly described herein, the present invention features a warming apparatus, and more particularly, a heating surface, such as a hot plate apparatus, adapted to warm a scented candle or other object resting thereon, wherein the heating surface comprises a number of additional features to enhance the candle burning experience. Although any object containing a substance, such as a wax or wax-like substance, is intended to be included within the scope of the present invention, for the purposes of discussion, a scented candle will be used throughout to represent the object of preference. This is not meant to be limiting in any way, but is meant to be used for illustrative purposes only.

The warming apparatus of the present invention is configured to include one or a combination of features, such as one or more light sources for illuminating the candle and/or the warming device, a cord-adjusting apparatus, and/or auxiliary attachment means for attaching decorative or functional items, such as seasonal or holiday oriented designs, various art and craft designs, etc., to the warming apparatus.

In one exemplary embodiment, the warming apparatus includes a heating surface or a hot plate and means for illuminating an object, such as a candle. Means for illuminating an object comprises a light source operable with the warming apparatus that functions to provide or simulate the same or similar visual effects as existing in a burning candle. Preferably, the light source is embedded within or near the heating surface so that the light may penetrate the liquefied substance within the container resting atop and in contact with and being heated by the heating surface. The heating surface may comprises a heat source of any known or desired means, such as a resistive heating device, halogen lighting, coil heating, etc. In a preferred embodiment, the heating surface is heated by means of a ceramic heating element. Ceramic heating elements are advantageous because they can generate adequate quantities of heat energy within a controlled temperature range.

The light source may be located internally or externally relative to the heating surface of the warming apparatus. As stated, in a preferred embodiment, the light source is embedded or otherwise disposed within the heating surface or other location of the hot plate in order to illuminate the candle (or some other type of container containing a wax or wax-like substance) through either the bottom surface or a side surface, or both, of the candle. In addition to, or instead of a light source disposed within the hot plate, one or more light sources may be located on or within the housing of the warming apparatus surrounding the hot plate in order to illuminate the candle through the sidewall of the candle container.

The light source can be adapted to provide a constant warm glow. Alternatively, the light source can be adapted to replicate or simulate the flicker and lighting of a burning candle. A combination of lights in various locations can be utilized in order to provide a multiplicity of lighting effects, such as a continuous warm background glow and/or intermittent flickering. The several different configurations and lighting effects are not all discussed herein as one ordinarily skilled in the art will recognize the possibilities.

The warming apparatus of the present invention further features an adjustable power cord apparatus. In one aspect, the adjustable power cord apparatus may be adapted to allow the user to alter the length of the cord extending from the housing of the warming apparatus. In another aspect, the user may be able to reposition the relative location of the power cord and where the power cord extends from the housing to account for varying locations of power outlets relative to the warming device. This also helps to prevent an excess of visible cord length. The adjustable cord apparatus itself preferably comprises a cord retention mechanism adapted to secure some or all of the electrical cord adjacent to, or within, the housing of the warming apparatus.

In one exemplary embodiment, the cord retention mechanism is designed to be concealed in a recess existing on the underside of the housing. Slots positioned around the perimeter of the underside of the housing may be included to provide varying exit points for the cord from the housing. The cord retention mechanism may be adapted to permit a user to coil or spool some or all of the cord around the retention mechanism such that the retained portion of the cord is not seen when the warming apparatus is in use. The cord retention mechanism may provide manual (e.g., by means of a stationary spool) or automatic spooling of the cord (e.g. a biased mechanism or device, such as a rotatable spring coil mechanism).

In yet another embodiment, the warming apparatus of the present invention may include auxiliary attachment means. The auxiliary attachment means is adapted to permit additional components and/or materials to be selectively coupled to the warming apparatus. In one embodiment, the auxiliary attachment means comprises a plurality of slots or recesses that are adapted to allow decorative face plates, covers, and similar items to be selectively attached to the warming apparatus as desired. These decorative face plates and covers are preferably interchangeable to allow the warming apparatus of the present invention to feature various designs, themes, and looks as desirable. Such slots or recesses may also accommodate one or more clips that can be used to hold a decorative sleeve around the candle, such as a transparent plastic sleeve having decorations printed thereon, a colored sleeve and/or a sleeve that has been cut or stamped so as to have various designs or reliefs.

Other features that may be incorporated within, or used in conjunction with, the warming devices according to the invention include, but are not limited to, the following: internal lighting means for illuminating the warming apparatus itself in addition to, or instead of, lighting the candle; a housing having a desired decorative shape (e.g., a tear drop); a housing that is transparent or that is of a desired color or design; interchangeable face plates; interchangeable decorative sleeves for different occasions (seasonal changes, holidays, birthdays, anniversaries or other special occasions); a non-stick coating for the hot plate (e.g., Teflon) to provide easy cleaning; plastic under the hot plate for a nonpermeable plate in between the lights; lighting features so that the warming device can function as a night light (e.g., it can remain illuminated even when not warming a candle); a built-in voltage adapter to accommodate different voltages around the world and obviate the need for an external voltage converter; changeable electric plugs to accommodate different outlets worldwide; a built in timer for automatically turning on and off the heating and/or lighting features; fan and fan vents to assist in heating taller, larger or hard to heat candles, as well as providing means for circulating the air to facilitate dissemination of the scented particles through the air; a heat focusing sleeve that can be used to focus or redirect heat from an oversized hot plate to an undersized candle, including interchangeable heat focusing sleeves that can accommodate a variety of differently-sized candles; dimming means for controlling the intensity of illumination from the lighting sources, wherein the dimming means may comprise a variable or adjustable heating surface to accommodate or allow for various amounts of escaping light; and a rheostat and/or thermostat for regulating the temperature of the heat emitted by the hot plate in order to maintain a desired temperature for a given type of candle wax.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 9, is not intended to limit the scope of the invention, as claimed, but is merely representative of the presently preferred embodiments of the invention.

The presently preferred embodiments of the invention will be best understood by reference to the drawings wherein like parts are designated by like numerals throughout.

The present invention features a warming apparatus. More particularly the invention features a hot plate apparatus adapted to warm an object, such as a scented candle or other object resting thereon. The apparatus can be configured to include one, or a combination of, features, such as one or more light sources for illuminating the candle and/or the warming device, a cord-adjusting apparatus, and/or attachment means for attaching decorative items to the warming apparatus.

While the following description details the preferred embodiment of the present invention warming apparatus, the disclosure herein is not meant to be limiting in any way. Indeed, one ordinarily skilled in the art will recognize other features and advantages not necessarily or specifically recited or recognized herein, but that fall within the scope of the invention as described and claimed.

In order to more succinctly set forth the advantages and functions of the present invention warming apparatus, the following disclosure will feature four focused areas of discussion as follows: 1) the warming apparatus and its functions; 2) the adjustable cord feature; 3) the means for illuminating or the light source; and 4) the attachment apparatus.

WARMING APPARATUS

Figure 1:
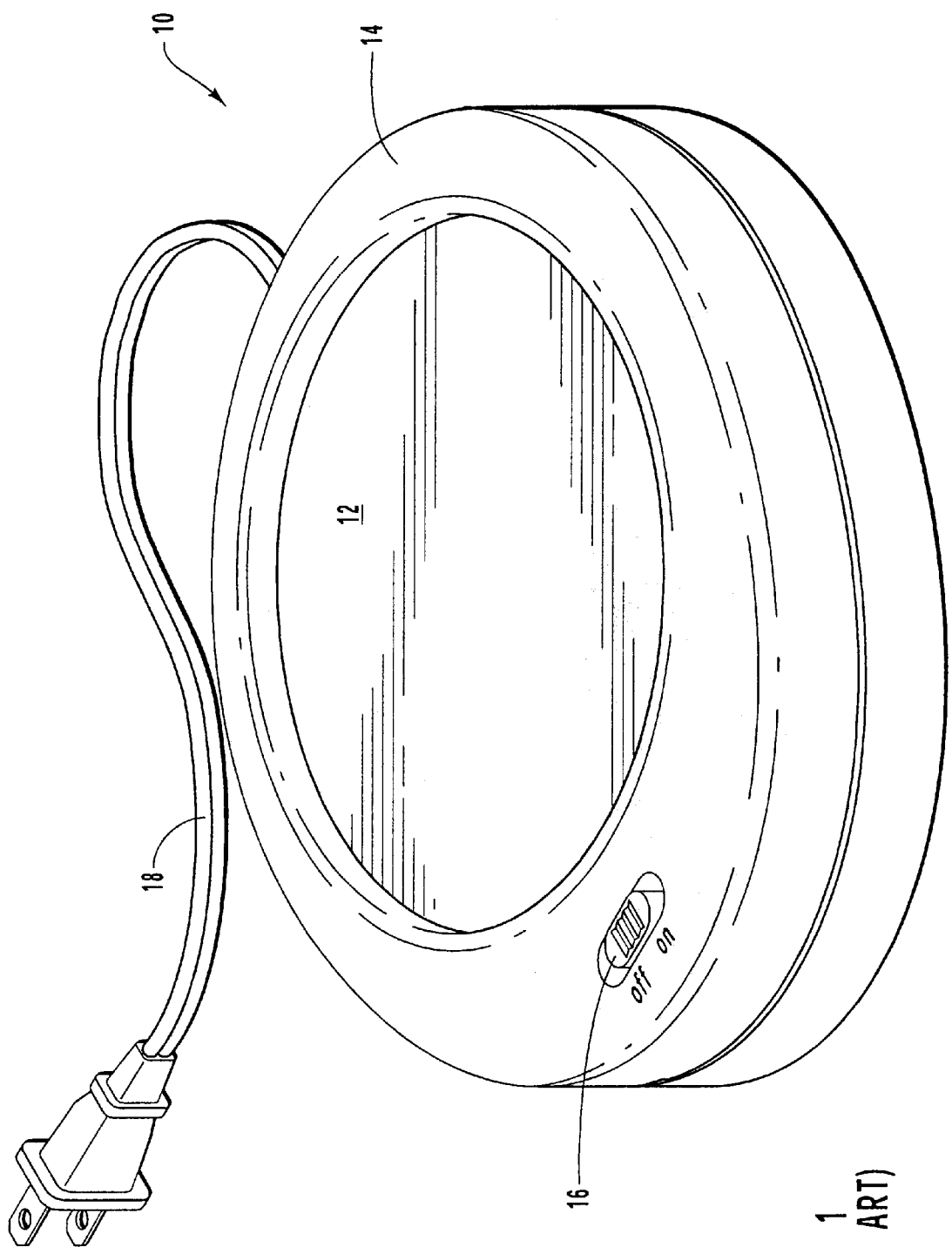
FIG. 1 is a perspective view illustrating a prior art warming apparatus.
Figure 2:
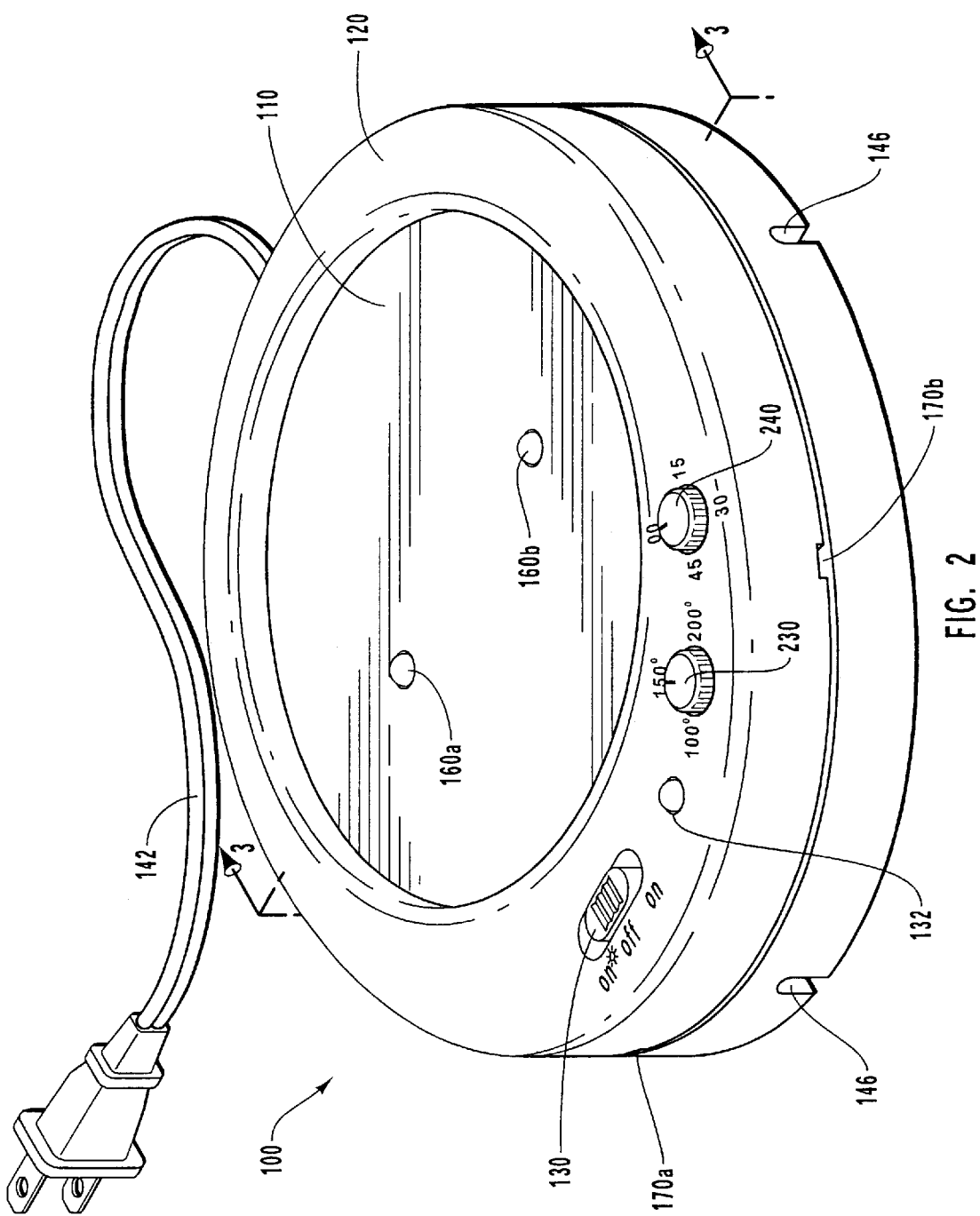
FIG. 2 is a top perspective view illustrating a warming apparatus according to the present invention that is able to illuminate a candle or other object resting thereon.

With reference now to FIG. 2 there is shown a warming apparatus 100 according to one embodiment of the present invention. In the illustrated embodiment, warming apparatus 100 comprises a heating surface (e.g. hot plate) 110, a housing 120, a switch 130, an adjustable cord apparatus 140, a light source 160, and attachment means 170. There is also shown an on/off LED 132 and a cord outlet 146. Warming apparatus 100 is configured to provide heat to an object or substance resting thereon.

While in the illustrated embodiment warming apparatus 100 has a generally circular or oval shape, any of a variety of configurations are possible. For example, warming apparatus 100 can be adapted to have a decorative shape, such as a tear drop or flower. The warming apparatus 100 can also be adapted to heat objects and substances having different sizes, properties, and configurations. In one embodiment the surface area of heating surface 110 is adapted to correspond with the bottom surface area of a small candle. In an alternative embodiment, a larger warming apparatus 100 is provided having one or more vents to heat the sides of a taller or more massive candle.

Heating surface 110 is adapted to transfer heat to an object or substance in contact therewith from a heating element (not shown). For example, heating element and heating surface 110 can warm an aromatic candle contained in a glass container. By providing additional heat to the candle, the aroma of the candle can be released without lighting the candle. Not only does this preserve the life of the candle, but can also reduce the fire hazard that can be caused by having a lit candle in a dwelling. The use of heating surface 110 is not limited to heating of aromatic candles. Heating surface 110 can also be used to heat other objects or substances, such as coffee mugs, tea cups, etc.

Housing 120 is adapted to provide a full or partial covering to internal circuitry associated with heating surface 110. Housing 120 provides an insulating covering to protect a user from inadvertent electrical shock or burn caused by touching the internal wiring or heating element associated with heating surface 110. Housing 120 can be comprised of a single unit, or two or more sections adapted to be coupled together. Housing 120 can also be adapted to provide features in addition to the covering of the internal circuitry. For example, housing 120 can be adapted with an annular flange surrounding the surface of heating surface 110. The annular flange would provide a mechanism for keeping an object from sliding off the surface of heating surface 110. Housing 120 can also provide decorative features to warming apparatus 100. For example, housing 120 can be adapted to receive a decorative faceplate having a custom design.

Switch 130 provides a method of actuating and deactivating warming apparatus 100. A variety of switch mechanisms can be utilized to actuate or deactivate heating element and heating surface 110. In the illustrated embodiment, switch 130 comprises a three-way switch. Switch 130 will be discussed in greater detail with reference to FIG. 7. On/off LED 132 operates in connection with switch 130. On/off LED 132 is utilized to provide a visual indication that heating surface 110 is actuated.

Figure 4:
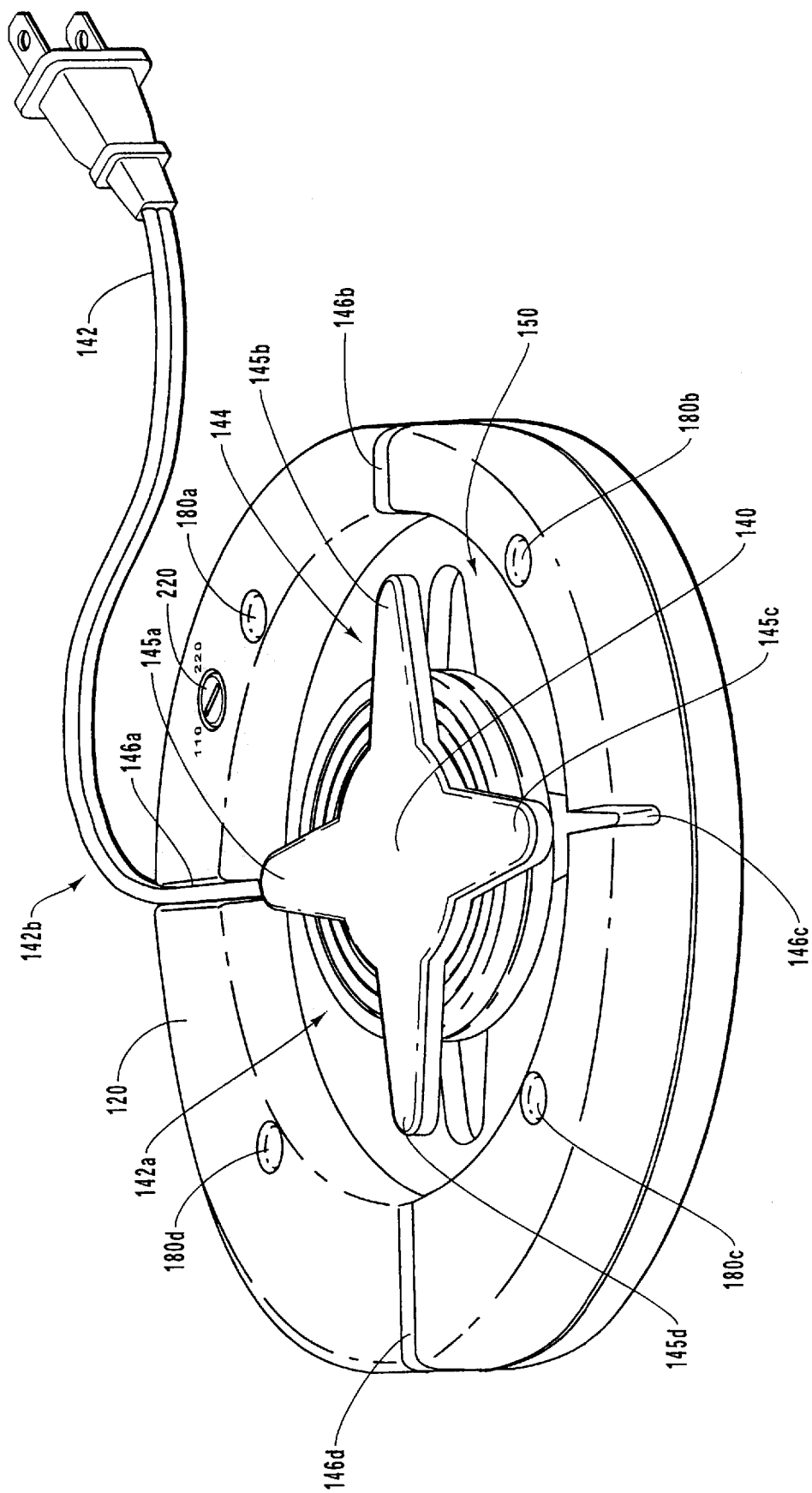
FIG. 4 is a bottom perspective view of the warming apparatus of FIG. 2 showing features that allow for adjustments to cord length and position relative to the warming apparatus housing.

With reference to FIG. 4, there is also provided an adjustable cord apparatus 140. Adjustable cord apparatus 140 is adapted to provide electricity to a heating element associated with heating surface 110 while allowing the user to alter the length of the electrical cord that is extending from the warming apparatus. Adjustable cord apparatus 140 can include a plurality of outlet slots 146. Outlet slots 146 allow the user to affix the electrical cord to housing 120. Outlet slots 146 provide alternative positions at which the cord can extend from the warming apparatus 100. The adjustable cord apparatus 140 will be discussed in greater detail with reference to FIGS. 4, 5a, 5b, and 6.

Light source 160 is adapted to provide illumination to an object or substance resting on heating surface 110 or housing 120. For example, light source 160 can illuminate a candle resting on heating surface 110. To provide illumination to the object or substance, light source 160 is adapted to be proximal to heating surface 110. Light source 120 can comprise one or more types of known lighting mechanisms. For example, in the illustrated embodiment, light source 120 comprises a first light emitting diode (LED) 160a and a second LED 160b.

It will be understood by one skilled in the art, that a variety of types and configurations of light source 160 can be utilized within the scope and spirit of the present invention. For example, light source 160 can comprise one or more incandescent or halogen bulbs. In the case of a halogen bulb, such may also be used to serve as heating means to heat heating surface 110. Light source 160 can be coupled to housing 120 or emanate from below heating surface 110. In one embodiment, light source 160 provides a focused illumination. In an alternative embodiment light source 160 is configured to wrap around the rim portion of housing 120. Light source can be adapted to illuminate an object resting on heating surface 110 (i.e. candle), an object resting on housing 120 (i.e. decorative cover,) or the warming apparatus 100 itself. In one embodiment, illumination of the warming apparatus can be provided independent of actuation of hot plate 100. This allows a user to selectively illuminate the warming apparatus 100, such that warming apparatus 100 can be employed as nightlight or decorative accent. Light source 160 will be discussed in greater detail with reference to FIGS. 7 and 8.

Attachment means or apparatus 170 is provided to permit additional components or materials to be coupled to the warming apparatus. In the illustrated embodiment, attachment means 170 comprises a plurality of slots, 170a and 170b, configured to allow a decorative cover to be attached to the warming apparatus. In one embodiment, the decorative cover is attached to warming apparatus 100 using tabs that are insertable into slots 170a and 170b. Attachment means 170 will be discussed in greater detail with reference to FIG. 8.

FIG. 2 further illustrates temperature switch 230 and timer 240. Temperature switch 230 provides for varying temperature control to heating surface 110. Timer 240 allows one to set the time at which heating element or heating surface 110 will be actuated. Timer 240 may be set to allow any length of time for the actuation of heating surface 110. Once the set amount of time elapses, timer 240 deactivates heating surface 110 and warming apparatus 100 shuts off. Each of these features provides desirable advantages as well as safety precautions.

Figure 3:
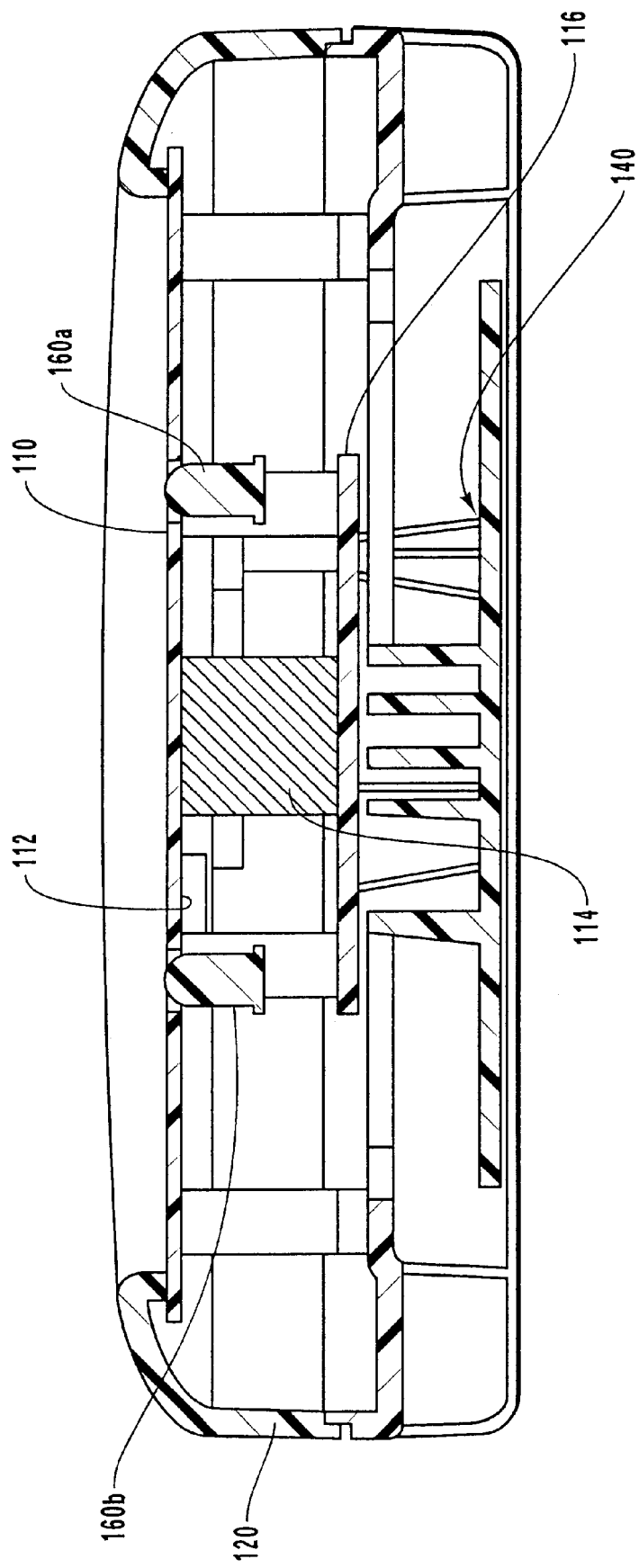
FIG. 3 is a cross-section view of the warming apparatus of FIG. 2 taken along cutting line 3—3.

FIG. 3 is a side cut-away view illustrating one embodiment of the warming apparatus of the present invention. There is shown heating surface 110, first and second LED's 160a and 160b, and adjustable cord apparatus 140. In the illustrated embodiment, heating surface 110 comprises a hot plate contacting surface 112, a heating element 114, and a circuit board 116. Hot plate contacting surface 112 comprises a metal, ceramic, or other material capable of conducting heat to an object or substance in contact therewith. Hot plate contacting surface 112 can be coated with Teflon, or another no-stick coating, to allow for easy cleaning.

Heating element 114 is coupled to the hot plate contacting surface 112. Heating element 114 is positioned below hot plate contacting surface 112 such that heating element 114 is enclosed by hot plate contacting surface 112 and housing 120. In the preferred embodiment, heating element 114 is comprised of a ceramic material due to the advantageous properties of ceramic heaters. In an alterative embodiment, heating element 114 is comprised of an element comprised of metal, wire coil, or other materials and constructions adapted to provide heat to hot plate contacting surface 112.

Circuit board 116 is adapted to provide logic functions required to actuate and deactivate heating surface 110 and first and second LEDs 160a and 160b. In one embodiment, circuit board 116 operates in connection with an adjustable rheostat, allowing a user to adoptively alter the temperature of hot plate contacting surface 112 in correspondence with the properties of the object or material resting thereon. For example, the rheostat can be configured to provide temperatures adapted to the particular temperature requirements of different candles (i.e. based on size of the candle or the type of container/wax.) Heating surface 110 can also include additional components. For example, in one embodiment a plastic coating is included under hot plate contacting surface 112. The plastic coating provides an impermeable seal to protect the internal circuitry of heating surface 110 and/or the light source. In another embodiment, a voltage adapter is included in the internal circuitry of heating surface 110 to allow the warming apparatus 100 to be used with different power sources of different voltages. In yet another alternative embodiment, a timer is included to control the functionality of heating surface 110 and/or the light source.

The cross sectional view of FIG. 3 illustrates the manner in which a light source can be coupled to heating surface 110. In the illustrated embodiment, first and second LEDs 160a,b are positioned such that the tip of first and second LEDs 160a,b fill apertures in hot plate contacting surface 112. The LED's can be integrally or separably coupled to hot plate contacting surface 112. FIG. 3 also illustrates an adjustable cord apparatus 140. Adjustable cord apparatus 140 is adapted such that the user can alter the length of the electrical cord that is extending from the warming apparatus. The adjustable cord apparatus 140 will be discussed in greater detail with reference to FIGS. 4 and 5.

ADJUSTABLE CORD APPARATUS

FIG. 4 is a bottom view illustrating one embodiment of the adjustable cord apparatus 140 of the present invention. In the illustrated embodiment, adjustable cord apparatus 140 comprises a cord 142, a cord retention mechanism 144, and cord outlets 146a–d. There is also shown housing recess 150 and scuff pads 180a–d. Adjustable cord apparatus 140 provides electricity to heating surface 110 while allowing the user to alter the length of the cord that is extending from warming apparatus 100.

Cord 142 comprises an electrical cord that is electrically connected to the internal circuitry of heating surface 110. Cord 142 provides a mechanism for providing electricity to heating surface 110. In the illustrated embodiment, cord 142 is an electrical cord of a type that is typically used with small electronic appliances. As will be understood by those skilled in the art, any electrical cord can be utilized that is suited to the requirements of warming apparatus 100. In one embodiment, electrical cord 142 is adapted to have changeable electrical plugs allowing the warming apparatus to be plugged into electrical outlets having different configurations.

Cord retention mechanism 144 is adapted to secure some or all of the cord proximate to housing 120. In the illustrate embodiment cord retention mechanism permits the user to coil cord 142. Cord retention mechanism 144 includes a plurality of projections 145a–d. Cord 142 is positioned such that a retained cord portion 142a is wrapped below projections 145a–d, while an extended cord portion 142b projects from the warming apparatus 100. Projections 145a–d hold the retained cord portion 142a in a tightly coiled configuration while allowing the user to alter the length of extended cord portion 142b by coiling, or uncoiling cord 142 from the cord retention mechanism 144.

Cord outlets 146a–d are adapted to receive cord 142. In one embodiment, cord outlets 146a–d comprise a plurality of slots adapted to permit the user to affix the cord to housing 120, thus providing alternative positions at which the cord can extend from warming apparatus 100. In an alternative embodiment, cord outlets 146a–d permit the user to vary the length of extended cord portion 142b.

In the illustrated embodiment, a housing recess 150 is provided to conceal adjustable cord apparatus 140. By concealing the adjustable cord apparatus 140, housing recess 150 permits the retained cord portion 142a and the cord retention mechanism 144 to be concealed when the warming apparatus 100 is in use. Thus, unneeded portions of cord 142 can be quickly and efficiently secured and concealed to provide a more tidy appearance to the warming apparatus 100. Scuff pads 180a–d are coupled to housing 120. Scuff pads 180a–d prevent scratches in surfaces on which warming apparatus 100 is placed. Scuff pads 180a–d can be adapted to provide a variety of benefits in addition to scratch prevention. For example, scuff pads can be adapted to provide slip resistance or separation between housing 120 and a counter top surface.

Also illustrated in FIG. 4 is voltage converter 220 allowing warming apparatus 100 to switch or alternate voltage levels, shown in FIG. 4 as either 110 or 220 volts. Voltage converter 220 compensates for varying circuitry and power levels existing within a location.

Figure 5B:
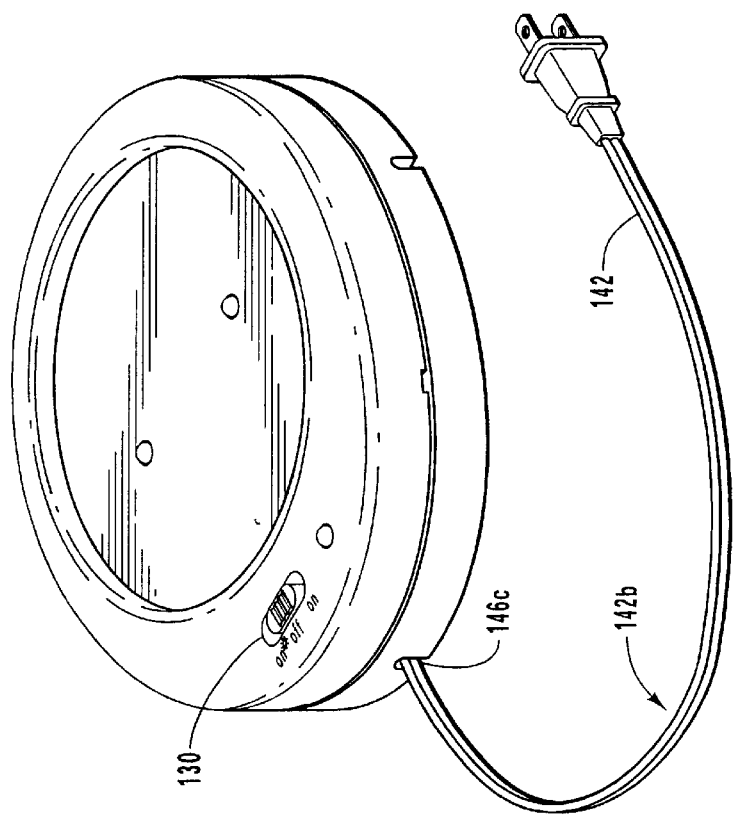
FIG. 5B is a perspective view of the warming apparatus of FIG. 2 with the cord positioned so that at least a portion of the cord extends from the front of the warming apparatus.
Figure 5A:
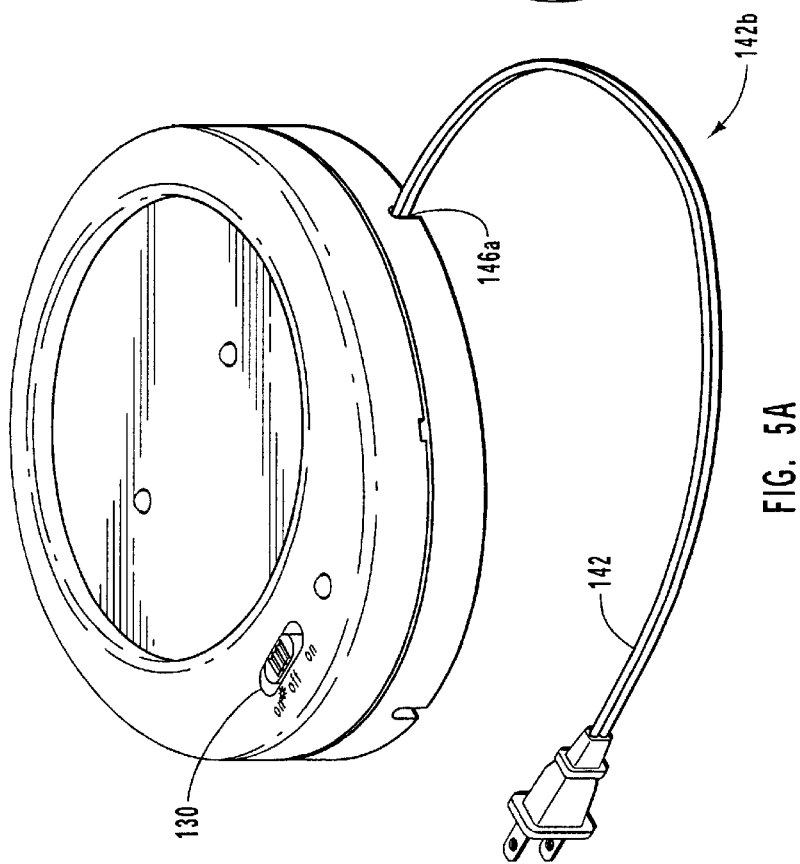
FIG. 5A is a perspective view of the warming apparatus of FIG. 2 with the cord positioned so that at least a portion of the cord extends from the right side of the warming apparatus rather than the rear as in FIG. 2.

FIGS. 5a and 5b are perspective views of warming apparatus 100 illustrating the way in which adjustable cord apparatus 140 can be used to vary the configuration and length of the cord extending from warming apparatus 100. With reference now to FIG. 5a, there is shown a configuration of warming apparatus 100 in which the extended cord portion 142b has a first length. The first length of extended cord portion 142b is a shorter length. The shorter cord length is accomplished by securing the majority of cord 142 proximate housing 120 utilizing cord retention mechanism 144. Cord 142 is affixed to housing 120 using cord outlet 146. Due to the position of cord outlet 146, cord 142 extends from warming apparatus 100 from a side different or opposite switch 130.

With reference now to FIG. 5b, there is shown a configuration of warming apparatus 100 in which the extended cord portion 142b has a second length. The second length of extended cord portion 142b is a longer length achieved by securing a minority of cord 142 proximate to housing 120 utilizing cord retention mechanism 144. Cord 142 is affixed to housing 120 using cord outlet 146c. Due to the position of cord outlet 146c, cord 142 extends from warming apparatus 100 from the side proximate switch 130. Thus, it can be seen that by utilizing adjustable cord apparatus 140 a user can alter the length of cord 142 extending from the warming apparatus.

Cord outlets 146a–d also allow the user to alter the configuration of warming apparatus 100 by permitting the user to alternate the position at which cord 142 extends from warming apparatus 100. By permitting the user to alter the length and configuration of cord 142 extending from warming apparatus 100, the user can secure unneeded lengths of electrical cord in a concealed fashion. The ability to secure a portion of cord 142 can be useful where the distance between the warming apparatus 100 and the electrical outlet is less than the length of cord 142. The adjustable cord apparatus 140 can also be useful for neatly storing cord 142 when the warming apparatus 100 is not in use.

Figure 6:
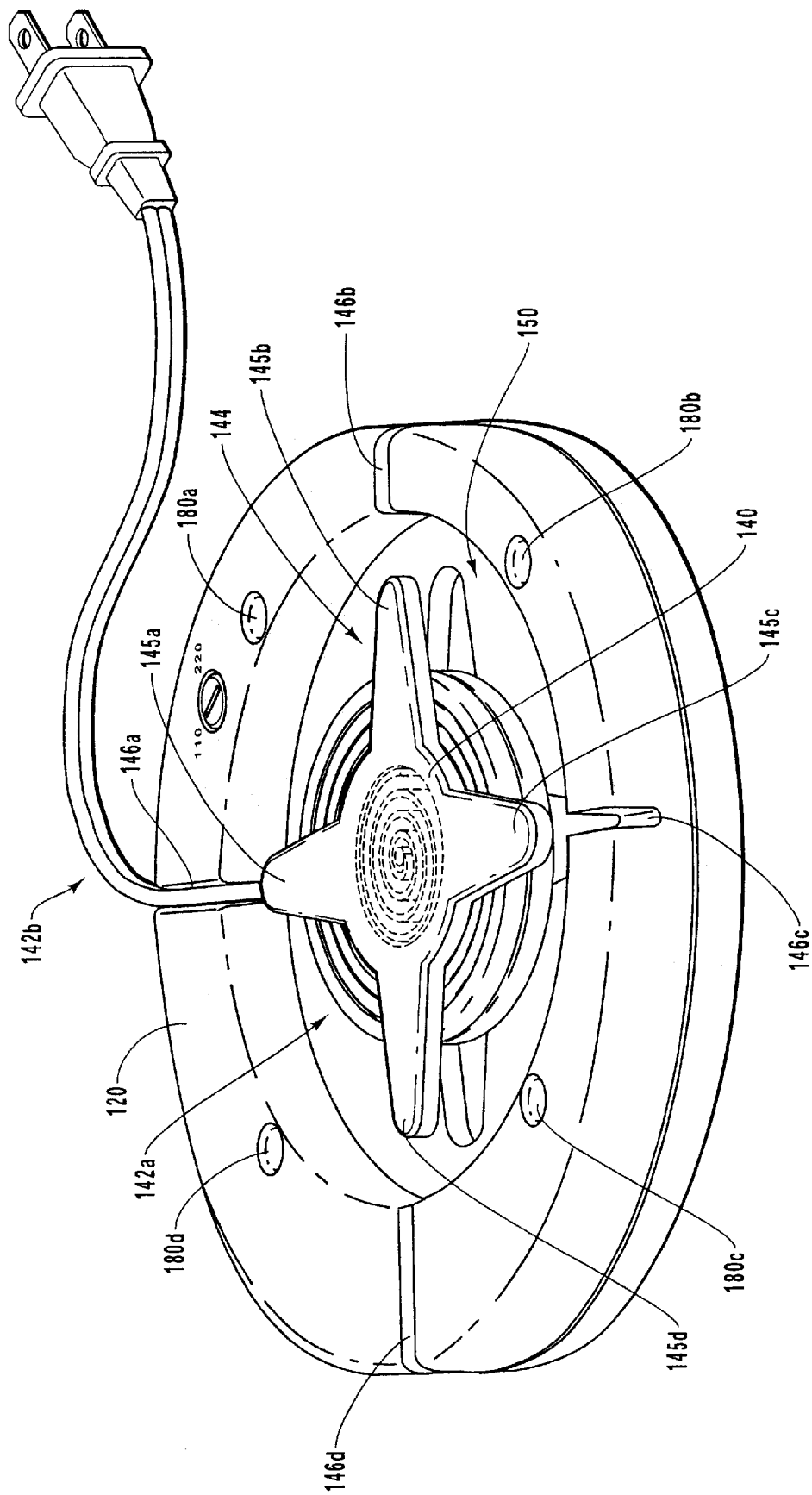
FIG. 6 illustrates an embodiment of an adjustable cord utilizing a rotatable spool with coiled spring to more precisely adjust the cord length as desired.

With reference now to FIG. 6, there is shown an alternative embodiment of adjustable cord apparatus 140. In the illustrated embodiment, the adjustable cord apparatus 140 comprises a spring or biasing coil mechanism. The spring coil mechanism is adapted to provide a method of effortlessly altering the length of cord 142 extending from warming apparatus 100. The spring coil is located internal to housing 120 of warming apparatus 100. This permits some, or all of, cord 142 to be secured and concealed internally in housing 120.

Essentially, spring coil mechanism rotates with respect to housing 120 to coil and uncoil cord 142. As cord 142 uncoils, the tension in the spring or biasing member increases having a tendency to want to re-coil and rotate in an opposing direction than taken to uncoil cord 142. However, a locking mechanism may be in place to prevent adjustable cord apparatus 140 from re-coiling until desired. If a shorter length of cord is needed, adjustable cord apparatus 140, and particularly spring coil mechanism, is actuated so that adjustable cord apparatus 140 is causes to rotate and re-coil or wind cord 142 to a desired length.

While alternative embodiments of adjustable cord apparatus 140 have been described with reference to FIGS. 4, 5a, 5c, and 6, it will be appreciated that additional embodiments of the adjustable cord apparatus can be utilized within the scope and spirit of the present invention.

ILLUMINATION MEANS OR LIGHTING SOURCE

Figure 7:
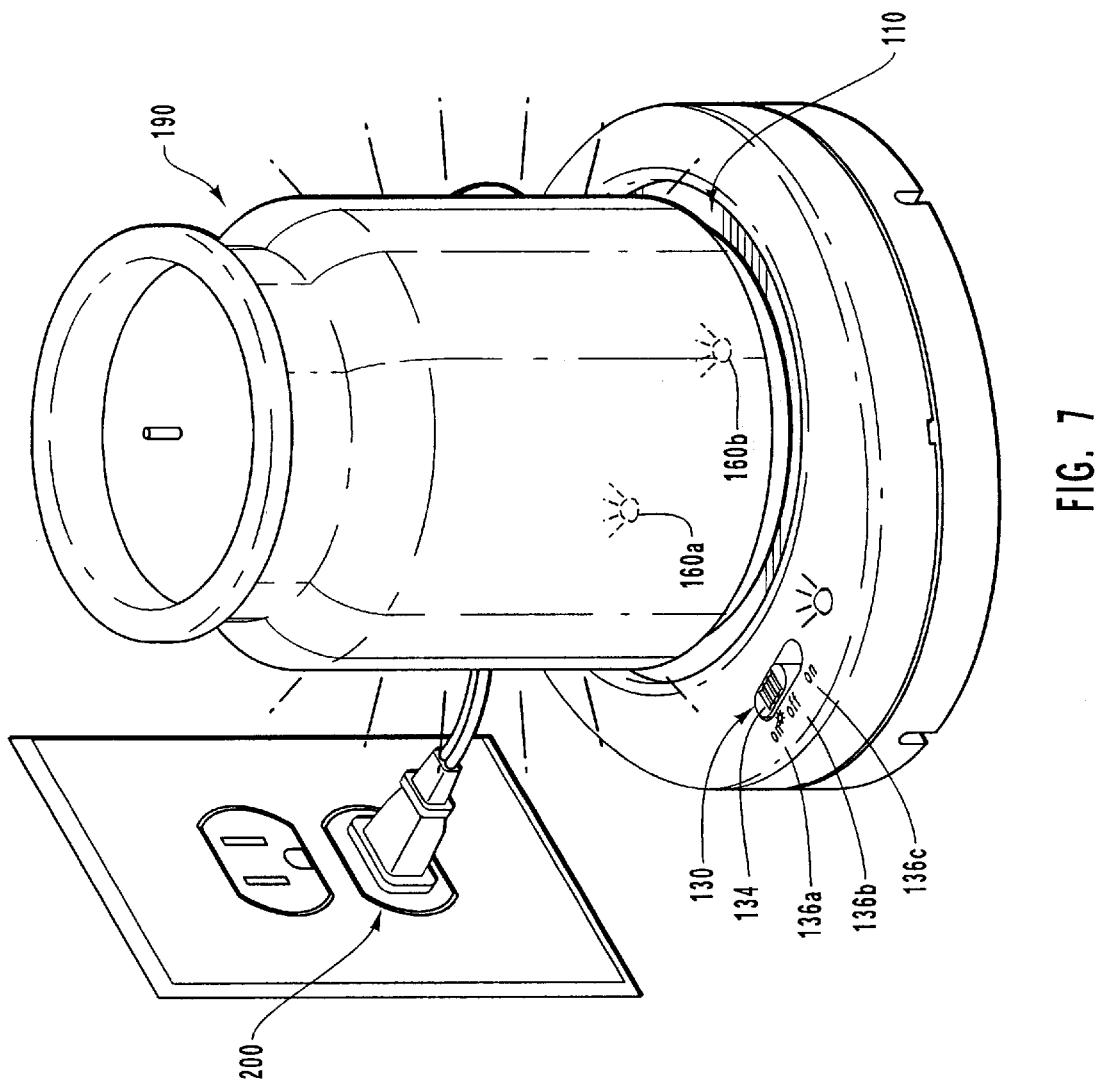
FIG. 7 is a perspective view of a warming apparatus according to the present invention illustrating the manner in which a light source disposed within the hot plate can be used to illuminate a transparent or translucent object resting on the hot plate.

FIG. 7 illustrates the manner in which a user can utilize illumination means or a light source 160 to illuminate internally, from within, or the outside of an object resting on heating surface 110. There is shown a heating surface 110, a switch 130, a candle 190, and a power source 200. As previously discussed, heating surface 110 is adapted to provide heat to an object resting thereon. Switch 130 provides a mechanism for actuating and deactivating heating surface 110. In the illustrated embodiment, switch 130 comprises a three-way switch having a switch knob 134. Switch knob 134 allows a user to control functionality associated with warming apparatus 100. When switch knob 134 is in a first position 136a, heating surface 110 is actuated and the light source is illuminated. When switch knob 134 is in a second position 136b, both heating surface 110 and the light source are deactivated. When switch knob 134 is in a third position 136c, heating surface 110 is actuated while the light source is deactivated. A light emitting diode (LED) 132 may be implemented to show or indicate that warming apparatus 100 is actuated and heating.

While switch 130 comprises a three-way switch, any variety of mechanisms for actuating and deactivating heating surface 110 and/or light source can be utilized. For example, one or more simple on/off switches can be utilized. Alternatively, a rheostat providing adjustable temperature functionality can be provided. Alternatively, the user can be required to actuate and deactivate the hot plate and/or the light source by simply attaching and detaching cord 142 to and from power source 200.

In the illustrated embodiment, switch knob 134 is in first position 136a. Accordingly, heating surface 110 is actuated and the light source is illuminated. Illumination of the light source causes illumination of the object resting on heating surface 110. Preferably, the illumination of the object is internal or from within to simulate various lighting effects of a burning candle. In the illustrated embodiment, the object resting on heating surface 110 is candle 190. Where the light source is integrally coupled to heating surface 110 (see FIG. 2), illumination of the light source is most readily apparent where the candle, or liquefied wax, is at least partially transparent. In an alternative embodiment of the present invention, the light source is coupled to either heating surface 110 or housing 120 such that opaque objects and/or substances resting on hot plate 120 are illuminated. Illumination of objects resting on warming apparatus 100 can be adapted to a variety of functions. For example, a candle can be illuminated to emphasize the color of the candle wax or to replicate a burning candle. In an alternative embodiment, the light source can be utilized to provide lighting for decorative objects and/or features associated with warming apparatus 100 (see FIG. 8). Illumination may be created to be emanate partially from the object or totally from the object. For example, partial illumination may be achieved by providing one or more lighting sources targeted or directed towards the object, as shown in FIG. 9. Total illumination, or illumination emanating from within the object, may be achieved by using lighting sources 160 as illustrated in FIG. 2.

ATTACHMENT APPARATUS

Figure 8:
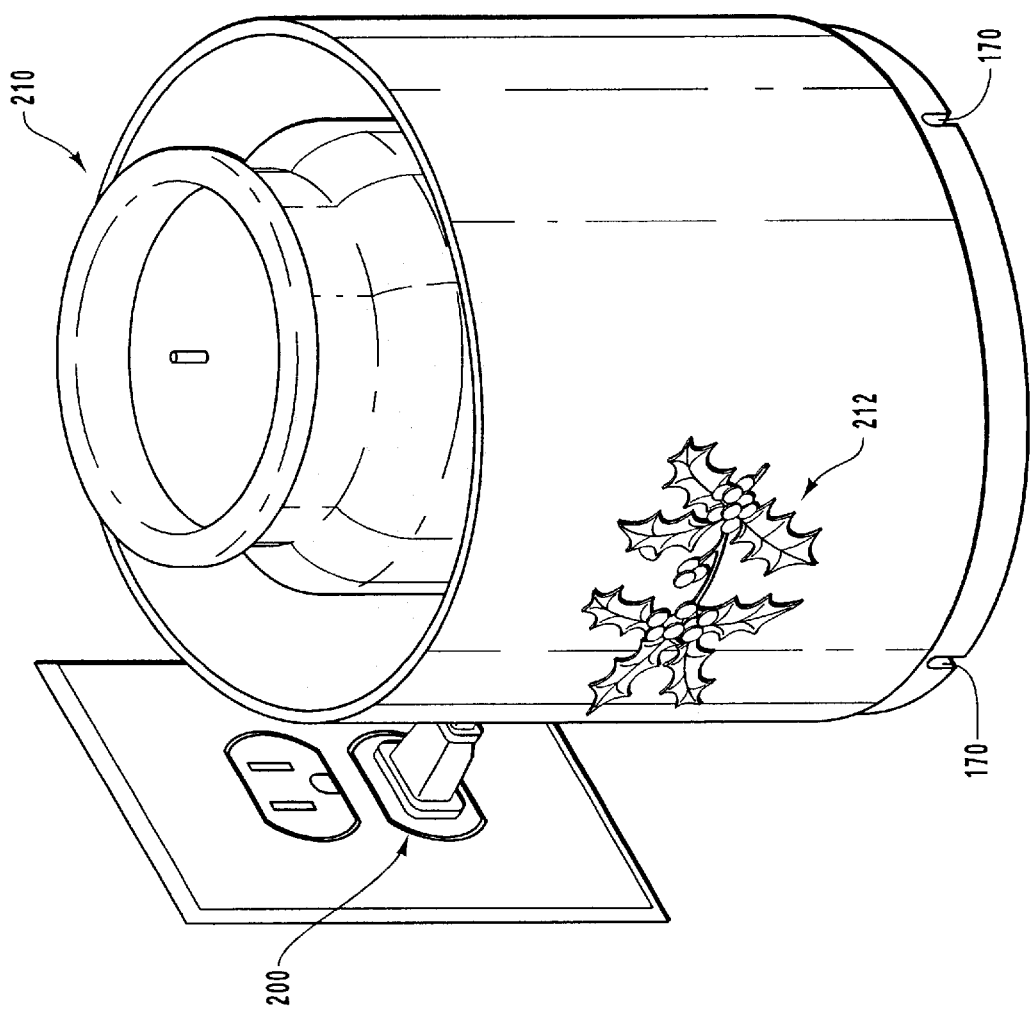
FIG. 8 depicts an embodiment of a warming apparatus according to the present invention in which a decorative sleeve is attached to the warming apparatus.
Figure 9:
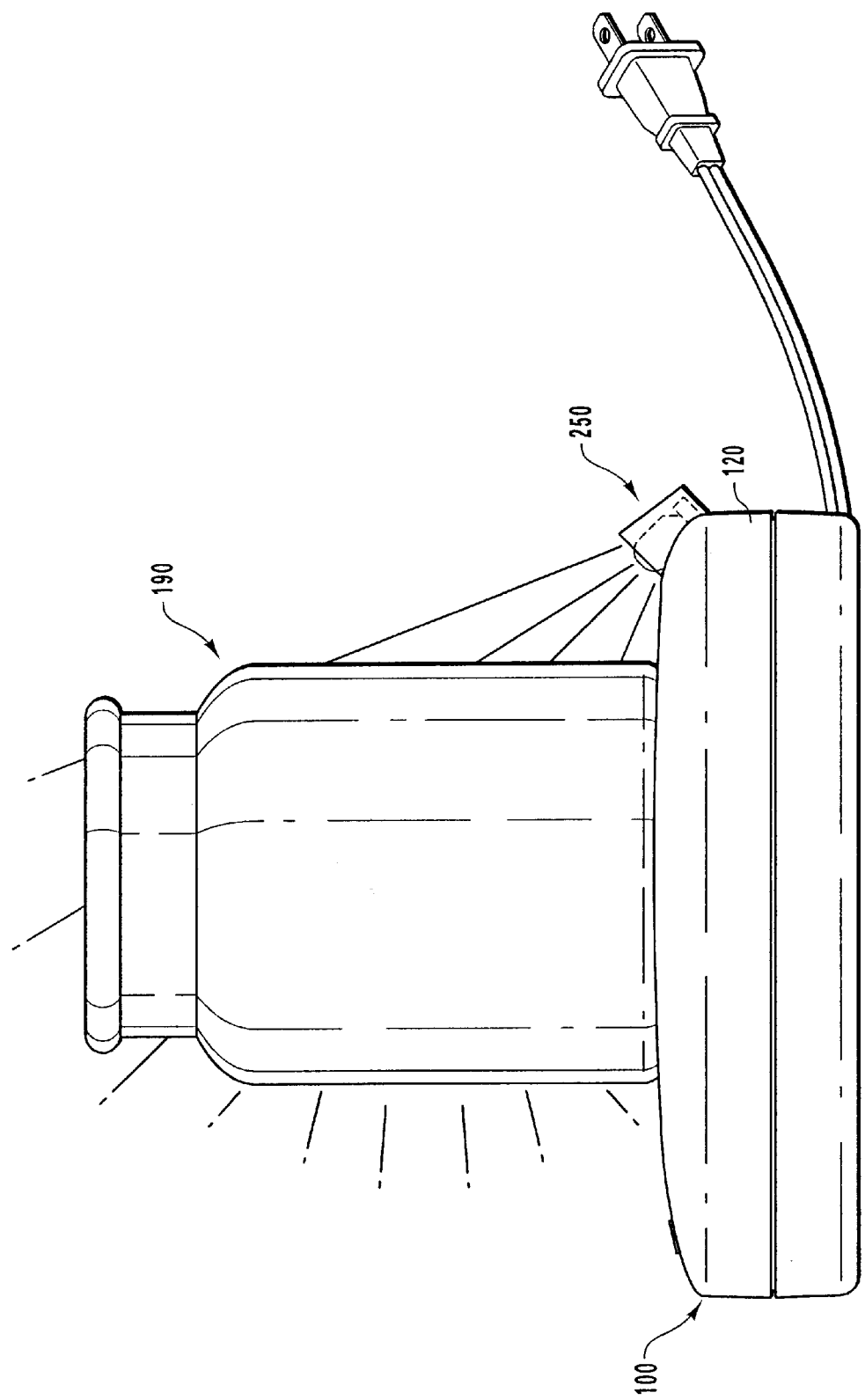
FIG. 9 depicts an embodiment of a warming apparatus in which the lighting source is located external to the hot plate so as to illuminate a transparent or translucent object from the side.

FIG. 8 shows one embodiment of the warming apparatus 100 of the present invention illustrating the method in which attachment means 170 can be utilized. Attachment means 170 permits additional and/or peripheral components, materials, objects, devices, covers, faceplates, light sources, etc. (collectively known as peripherals) to be coupled or interchangeably coupled to warming apparatus 100. In the illustrated exemplary embodiment, attachment means 170 comprises a plurality of slots 170a and 170b configured to allow a peripheral to be attached to warming apparatus 100. Slots 170a and 170b are integrally coupled to housing 120. Slots 170a and 170b are configured to receive corresponding tabs included on the peripheral. Slots 170a and 170b and tabs of the peripheral allow the peripheral to be selectively attached and removed from warming apparatus 100.

The slot and tab assembly described herein and shown in the drawings is not meant to be limiting in any way. As will be recognized by those skilled in the art, attachment means 170 is not limited to the configuration of the illustrated embodiment. A variety of configurations and mechanisms can be employed in scope and spirit of the present invention. For example, attachment means 170 may comprise one or more clips configured to allow materials or modules to be attached to the warming apparatus, or attachment means 170 may comprise other various known devices, structures, assemblies, etc. designed to allow one or more peripherals to be removably coupled to warming apparatus 100. For example, warming apparatus 100, and particularly attachment means 170, may comprise snaps, Velcro®, a tongue and groove assembly, a snap-fit extension and receiver assembly, threading, an interference fit assembly, or any other known and obvious means capable of removably coupling a peripheral item to the warming apparatus.

As stated, warming apparatus 100 is designed to accept several different types of peripherals through use of attachment means 170. In one exemplary embodiment, warming apparatus 100 is adapted to receive one or more face plates thereon. The face plates are preferably interchangeable in order to accommodate the changing of several themes or to be adaptable to different environments, etc. in which warming apparatus 100 may be placed. However, if desirable, these face plates may be fixed or rigidly attached. Moreover, the face plates may comprise any color, shape, wording, graphic, or texture as desirable. For example, the several face plates may comprise themes corresponding to the several holidays existing throughout the year, such as Christmas, Thanksgiving, Halloween, and Valentine's Day, or may comprise various designs, colors, and/or patterns to match the interior design of the particular environment in which warming apparatus 100 is placed. Essentially, the present invention contemplates the ability to alter its physical appearance and design through the interchanging of one or more detachable face plates.

None of the peripherals described herein interfere with the normal operation of warming apparatus 100, but rather will serve to complement both the aesthetics and the functionality of warming apparatus 100, either by making it more adaptable to a particular environment, or by providing a more desirable experience, or by increasing the illuminating characteristics of the apparatus, with these not meant to be limiting.

In another exemplary embodiment, shown in FIG. 8, warming apparatus 100 is adapted to receive a peripheral in the form of decorative cover 210. Decorative cover 210 may include a cover design 212 to enhance the aesthetics of the cover. The configuration of decorative cover 210 can include a variety of designs and colors. For example, the decorative cover can have a uniform opaque, variable transparent, or semitransparent design, or any other conceivable configuration. As shown, decorative cover 210 is comprised primarily of an opaque material.

Cover design 212 may be added to lend aesthetic ornamentation to decorative cover 210. As shown in FIG. 8, the portion of decorative cover 210 corresponding to cover design 212 comprises an aperture or transparent material allowing the light source to provide a backlight to accent or highlight cover design 212. The light source and the peripheral, namely the cover and cover design, can be utilized to achieve a variety of different aesthetic features. In one exemplary embodiment, a decorative cover configured to substantially cover a candle resting on the hot plate is affixed to the warming apparatus utilizing the attachment apparatus. The light source is adapted to provide a flickering illumination, thus lending the impression that the candle is lit.

In yet another exemplary embodiment, warming apparatus 100 is adapted to receive a peripheral in the form of one or more crafts and/or modules. Example crafts may include such items as flowers, wreaths, shams, skirts, etc. Modules may include any device or structure or item that protrudes out from warming apparatus 100 and that is removably attached to warming apparatus 100 using attachment means 170. For example, during Christmas, one may wish to attach a candy holder, a bell, an ornament, etc.; or, one may desire to attach a figurine, etc.; or, one may wish to attach exterior lights. These are merely examples as one ordinarily skilled in the art will recognize the countless peripheral modules or objects that may be attached to warming apparatus 100.

In yet another exemplary embodiment, the present invention further contemplates the attachment or coupling of a heat condenser to warming apparatus 100 using attachment means 170. The heat condenser is designed to focus heat from heating surface 110 to an object proximate heating surface 110. The heat condenser can be utilized, for example, where a the surface area of the bottom of a candle is much smaller than the surface area of contacting surface 112. The heat condenser focuses the heat emanating from the larger contacting surface 112 to the candle.

FIG. 9 illustrates one embodiment of warming apparatus 100 in which lighting source 250 is located external to heating surface so as to illuminate a transparent or translucent object from the side. One or more lighting sources 250 may be employed to provide various ambient lighting effects.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A warming apparatus for warming an object in contact therewith, said warming apparatus comprising:
    a housing adapted to receive said object;
    heating means associated with said housing, said object juxtaposed to said heating means for selectively heating said object; and
    lighting means disposed on at least one of said housing and said heating means, for selectively illuminating the interior of said object to create one or more lighting effects emanating from said object.

2. The warming apparatus as defined in claim 1, wherein said heating means comprises a heat-emitting surface disposed on said housing.

3. The warming apparatus as defined in claim 1, wherein said heating means comprises a heat-emitting surface disposed partially within said housing.

4. The warming apparatus as defined in claim 2, wherein said heat-emitting surface is selectively heated by means of at least one resistive heating element.

5. The warming apparatus as defined in claim 4, wherein said resistive heating element comprises a ceramic heating element.

6. The warming apparatus as defined in claim 2, wherein said lighting means comprises at least one light source disposed within said heat-emitting surface.

7. The warming apparatus as defined in claim 2, wherein said lighting means comprises at least one light source disposed on said housing external to said heat-emitting surface.

8. The warming apparatus as defined in claim 1, wherein said lighting means comprises at least one light emitting diode.

9. The warming apparatus as defined in claim 1, wherein said lighting means comprises at least one incandescent or fluorescent bulb.

10. The warming apparatus as defined in claim 1, further comprising at least one light source adapted to selectively illuminate said housing.

11. The warming apparatus as defined in claim 1, further comprising attachment means for selectively allowing a peripheral to be attached to said housing.

12. The warming apparatus as defined in claim 11, wherein said attachment means comprises one or more devices, structures, assemblies selected from the group consisting of clips, snaps, Velcro®, a tongue and groove assembly, a snap-fit extension and receiver assembly, threading, an interference fit assembly, and any other known and obvious means capable of removably coupling said peripheral item to said warming apparatus.

13. The warming apparatus of claim 1, further comprising a peripheral removably attachable to said housing.

14. The warming apparatus of claim 13, wherein said peripheral comprises an interchangeable face plate.

15. The warming apparatus of claim 13, wherein said peripheral comprises a decorative cover or sleeve.

16. The warming apparatus of claim 13, wherein said peripheral comprises a module object.

17. The warming apparatus of claim 13, wherein said peripheral comprises a craft object.

18. A warming apparatus adapted for selectively heating and illuminating a substance contained within a container, said warming apparatus comprising:
    a heating surface adapted for selectively supporting and heating said container and said substance contained therein as said container is resting on said heating surface;
    a housing associated with and supporting said heating surface;
    a heating element associated with and supported by said housing, said heating element adapted to selectively supply heat to said heating surface; and
    one or more light sources located within said heating surface adapted for selectively illuminating the interior of said substance and said container to create one or more lighting effects emanating from said substance and said container.

19. The warming apparatus of claim 18, wherein said substance is a wax or wax-like substance.

20. The warming apparatus of claim 19, wherein said container and said wax comprises a candle.

21. The warming apparatus of claim 18, wherein said light source is embedded within one or more recessed portions of said heating surface.

22. The warming apparatus of claim 18, wherein said heating surface is sized and configured in order to accommodate and selectively heat a variety of differently sized containers.

23. The warming apparatus of claim 18, wherein said heating surface is coated with tetrafluoroethylene.

24. The warming apparatus of claim 18, wherein said heating element comprises a ceramic heating element.

25. The warming apparatus of claim 18, wherein said one or more light sources comprise LEDs.

26. The warming apparatus of claim 18, wherein said housing extends laterally beyond a perimeter of said heating surface.

27. The warming apparatus of claim 18, further comprising one or more external light sources located on said housing and adapted for selectively illuminating said candle through a side wall thereof.

28. The warming apparatus of claim 18, further comprising further comprising attachment means for selectively allowing a peripheral to be attached to said housing.

29. The warming apparatus of claim 18, further comprising a peripheral removably attachable to said housing.

30. The warming apparatus of claim 29, wherein said peripheral comprises an interchangeable face plate.

31. The warming apparatus of claim 29, wherein said peripheral comprises a decorative cover or sleeve.

32. The warming apparatus of claim 18, further comprising a power cord connected to said housing for selectively supplying electrical power to said heating element.

33. The warming apparatus of claim 32, further comprising means for adjusting a length of said power cord, said means for adjusting concealed within a recess in said housing and adapted to receive and store said power cord thereon.

34. The warming apparatus of claim 33, wherein said means for adjusting said power cord comprises a cord retention mechanism.

35. The warming apparatus of claim 34, wherein said cord retention mechanism comprises a stationary spool adapted to accept said power cord as said power cord is wound around said spool to selectively lengthen or shorten said power cord.

36. The warming apparatus of claim 34, wherein said cord retention mechanism comprises an adjustable power cord apparatus in the form of a rotatable biased spool mechanism comprising a rotatable spring loaded spool designed to coil and uncoil said power cord via the force induced rotation of said spool.

37. The warming apparatus of claim 32, wherein said housing includes a plurality of recesses adapted so as to permit selective repositioning of a location of said power cord respective to said housing.

38. The warming apparatus of claim 18, further including at least one light source located internally within said housing and adapted for selectively illuminating said housing.

39. The warming apparatus of claim 18, further including a power switch for selectively supplying and terminating electrical power to at least one of said heating element and said one or more light sources.

40. The warming apparatus of claim 18, further comprising a timer adapted for selecting a desired time duration during which at least one of said heating element and said one or more light sources are supplied with electrical power.

41. The warming apparatus of claim 18, further comprising a temperature adjustor to selectively adjust and control the temperature of said heating surface.

42. The warming apparatus of claim 18, further comprising a voltage converter adapted for selectively altering the voltage of electrical power that is supplied to said warming apparatus.

43. The warming apparatus of claim 18, further comprising auxiliary attachment means adapted to permit additional peripherals to be selectively coupled to said warming apparatus.

44. The warming apparatus of claim 43, wherein said auxiliary attachment means comprises one or more slots around a perimeter of said housing to allow attachment of said peripherals.

45. The warming apparatus of claim 43, wherein said peripherals comprise one or more of decorative face plates, decorative sleeves, crafts, modules, and external lights.

46. The warming apparatus of claim 18, wherein said housing comprises one or more decorative shapes.

47. The warming apparatus of claim 18, wherein said housing is transparent.

48. The warming apparatus of claim 18, wherein said housing comprises one or more decorative colors.

49. The warming apparatus of claim 18, further comprising a plastic membrane disposed beneath said heating surface, thus providing a non-permeable plate in between said lighting source.

50. The warming apparatus of claim 18, further comprising blower means adapted to circulate and disseminate any scented particles throughout the surrounding air and to facilitate heating of said substance and said container.

51. The warming apparatus of claim 18, further comprising a heat focusing sleeve used to focus or re-direct heat from said heating surface to said container.

52. The warming apparatus of claim 18, further comprising dimming means designed to accommodate and control the intensity of illumination.

53. The warming apparatus of claim 52, wherein said dimming means comprises an adjustable heating surface.

54. A warming apparatus adapted for selectively heating and illuminating a candle comprising:
   heating means for selectively heating said candle in contact therewith;
   housing means for supporting said heating surface;
   lighting means, disposed on or within at least one of said heating means and said housing means, for selectively illuminating at least one of a base or side wall of said candle in contact with said heating means, and for selectively illuminating the interior of said candle to created simulated lighting effects emanating from said candle; and
   switching means for selectively providing electrical power to at least one, and preferably both, of said heating means and said lighting means.

55. The warming apparatus of claim 54, further comprising a power cord electrically connected to said housing for selectively supplying power to said heating element.

56. The warming apparatus of claim 45, wherein said warming apparatus further comprises cord adjustment means for selectively extending and retracting said power cord and for selectively repositioning said power cord relative to said housing means.

57. The warming apparatus of claim 54, further comprising attachment means for allowing the attachment of one or more peripherals to said housing.

58. A method for heating and illuminating a scented substance, said method comprising the steps of:
   providing a scented substance disposed within at least a partially transparent container;
   causing said container to be received by a warming and illuminating apparatus;
   heating, with a heating means, in a repeated and continuous manner, at least a portion of said container in order to cause said scented substance to emit a scent therefrom; and
   illuminating, with lighting means, in a continuous manner, at least a portion of said scented substance by passing light through said underside of said container to create simulated lighting effects emanating from said substance and said container.

59. The method for heating and illuminating a scented substance of claim 58, further comprising the step of placing a decorative sleeve around said transparent container in order to provide decoration to said transparent container.

60. The method for heating and illuminating a scented substance of claim 58, further comprising the step of placing a heat focusing sleeve around a bottom portion of said transparent container in order to collect and transfer heat to said substance that would otherwise be dissipated into the air.

61. The method for heating and illuminating a scented substance of claim 58, wherein said scented substance comprises a scented candle.

62. The method for heating and illuminating a scented substance of claim 58, wherein said warming and illuminating apparatus comprises:
   a housing adapted to receive said container;
   heating means associated with said housing, said container juxtaposed to said heating means for selectively heating said container; and lighting means disposed on at least one of said housing and said heating means, for selectively illuminating the interior of said object to create one or more lighting effects emanating from said object.

63. The method for heating and illuminating a scented substance of claim 62, further comprising the step of altering the appearance of said warming and illuminating apparatus by removably coupling one or more peripherals to said housing.

64. A warming apparatus for warming an object in contact therewith, said warming apparatus comprising:

a housing adapted to receive said object;

heating means associated with said housing, said object juxtaposed to said heating means for selectively heating said object; and a lighting source disposed on and wrapping around a perimeter rim portion of at least one of said housing and said heating means, said lighting source encircling a portion of said object for selectively illuminating said object.

\* \* \* \* \*